United States Patent [19]

Pike

[11] Patent Number: 4,662,892

[45] Date of Patent: May 5, 1987

[54] HAIR DYE COMPOSITION

[75] Inventor: Barry G. Pike, Surrey, England

[73] Assignee: Lever Brothers Company, New York, N.Y.

[21] Appl. No.: 591,722

[22] Filed: Mar. 21, 1984

Related U.S. Application Data

[63] Continuation-in-part of Ser. No. 413,110, Aug. 30, 1982, abandoned.

[30] Foreign Application Priority Data

Sep. 3, 1981 [GB] United Kingdom ............... 8126700

[51] Int. Cl.$^4$ .............................................. A61K 7/13
[52] U.S. Cl. ..................................... 8/410; 8/411; 8/412
[58] Field of Search ........................... 8/410, 411, 412

[56] References Cited

U.S. PATENT DOCUMENTS 4,125,367 11/1978 Bugaut et al. ............................ 8/411
4,268,264 5/1981 Grollier et al. ......................... 8/412

FOREIGN PATENT DOCUMENTS 2501862 7/1975 Fed. Rep. of Germany .......... 8/412
1012793 12/1965 United Kingdom .

OTHER PUBLICATIONS

Venkataraman "The Chemistry of Synthetic Dyes", vol. 5, pp. 475–505, 1971.
The Merck Index (8th ed.) p. 894.

Primary Examiner—Albert T. Meyers
Assistant Examiner—John M. Kilcoyne
Attorney, Agent, or Firm—Milton L. Honig; James J. Farrell

[57] ABSTRACT

A composition for use in the dyeing of keratinous fibres, particularly human hair, in order to produce a true dark black color, comprises an aqueous, substantially oxygen-free solution of the dye-precursors 2-methoxy-p-phenylenediamine and 2,4-diaminophenol, the composition having a pH value of from 6 to 12. The molar concentration of one dye precursor to the other is preferably from 1:10 to 10:1, and together they form from 0.25 to 15% by weight of the composition. Optionally, the composition can also contain a detergent and/or a thickening agent.

14 Claims, No Drawings

HAIR DYE COMPOSITION

This application is a continuation-in-part of application Ser. No. 413110 filed Aug. 30, 1982 now abandoned.

The invention relates to compositions for dyeing keratinous fibres, and more particularly to hair colorants.

For almost a century, p-phenylenediamine and p-toluylenediamine have both been recognized as primary intermediates in the dyeing of the hair. When mixed with hydrogen peroxide and applied to the hair, a proportion of the mixture migrates into the hair shaft and there reacts to form a permanent color. However, this procedure suffers from three disadvantages: firstly, the need to keep the intermediate and oxidizing agent separate until immediately prior to use, secondly, the need to mix the intermediate and oxidizing agent properly immediately prior to use and, thirdly, the risk that excess oxidizing agent might cause damage to the hair if too little intermediate is employed, or if mixing of intermediate and oxidizing agent is incomplete.

Certain substituted p-phenylenediamines, notably 2-methoxy-p-phenylenediamine, also known as 2,5-diaminoanisole, have been shown, for example in British Patent Specification No. 1,012,793, to be useful as dye intermediates in the dyeing of hair or wool, particularly in the presence of hydrogen peroxide, when a grey color was obtained.

Certain other substituted benzene compounds such as 2,4-diaminophenol have also been known for many years as dye intermediates in the dyeing of hair by the formation of a permanent color within the hair shaft after reaction with atmospheric oxygen. This principle is well established and is discussed, for example in Venkataraman K, (1971), "The Chemistry of Synthetic Dyes", Volume 5 at page 475 et seq., and particularly on page 497, where it is reported that a red-brown color was obtained with 2,4-diaminophenol.

Leon et al in German Patent No. 2,501,862 reports an auto-oxidizable dye comprising a p-phenylenediamine and a monosubstituted catechol. Coupling agents such as 2,4-diaminophenol can be added to this dye mixture. Medium brown hair shades are achievable with this particular coupling agent. A rainbow of other colors were noted with combinations of the three component system. Certain unspecified combinations provided nearly black shades.

Inspite of the considerable amount of research which has been conducted in this field, it has hitherto not been possible to provide a system based on an autoxidation reaction which will impart to living human hair, within a short contact time, a true dark black color.

We have now, however, discovered that a mixture of 2-methoxy-p-phenylenediamine and 2,4-diaminophenol can successfully be employed as dye precursors to impart a true dark black color to the hair, in the absence of a peroxide commonly used as an oxidizing agent in the dyeing of hair.

Furthermore, we have shown that the addition of either p-phenylenediamine or p-toluylenediamine to a mixture of 2-methoxy-p-phenylenediamine and 2,4-diaminophenol does not further enhance the dyeing operation nor do they influence the intenseness of the black color obtained. Mono-substituted catechols, as described in Leon et al, are neither required to achieve true dark black shades nor desirable components of the instant invention.

Accordingly, the invention provides a composition for use in the dyeing of keratinous fibres to produce a true dark black color, which comprises an aqueous, substantially oxygen-free solution of 2-methoxy-p-phenylenediamine and 2,4-diaminophenol, the composition having a pH value of from 6 to 12.

It should be explained that "keratinous fibres" are fibres having the basis of the protein keratin. Although animal hair such as wool is an example of "keratinous fibres" and can accordingly be dyed using compositions of the invention, the invention herein is described and illustrated for convenience in terms of human hair which is a further example of "keratinous fibres". The invention is furthermore applicable both to "keratinous fibres", such as hair on the human head, or to wigs and hair pieces made from human hair.

The 2-methoxy-p-phenylenediamine and the 2,4-diaminophenol, hereinafter referred to as "the dye precursors", together form from 0.25 to 15%, preferably from 1 to 10% by weight of the composition. Dye precursors other than 2-methoxy-p-phenylene-diamine and 2,4-diaminophenol, including mono-substituted catechols, are absent from these compositions; they are neither necessary nor desirable.

If less than 0.25% by weight of the dye precursor mixture is employed, then the composition is unlikely to dye hair a true dark black color, whereas if more than 15% by weight of the dye precursor mixture is employed, it is unlikely that the depth of the black color produced in the hair will be further increased beyond that obtained when up to 15% by weight of the precursors is employed.

The minimum concentration of each dye precursor to be employed will depend on the mole ratio of each, and on the total concentration of both dye precursors in the composition.

The molar ratio of 2-methoxy-p-phenylenediamine to 2,4-diaminophenol in the composition is accordingly generally from 1:10 to 10:1, the preferred molar ratios being from 1:5 to 1:3, ideally 3:1 to 1:1.

If the dye precursors are employed at concentrations whose molar ratio are outside of the range 1:10 to 10:1, it is unlikely that a good true dark black color will be achieved.

The concentration of each dye precursors in the composition is generally from 0.1 to 14.9%, preferably from 0.5 to 10% and most preferably from 1 to 8% by weight.

The 2-methoxy-p-phenylenediamine is conveniently employed in the form of its sulphate-monohydrate (molecular weight: 254) as supplied for example by Aldrich Chemicals Limited. The 2,4-diaminophenol is conveniently employed in the form of its dihydrochloride salt (molecular weight: 197), as supplied for example by Koch Light Limited. When the pH of the composition is adjusted to a value from 6 to 12, these salts will give rise to the respective dye precursor bases.

The compositions according to the invention should be substantially free from oxygen in order to prevent oxidation of the dye precursors taking place before application to the hair. It is accordingly apparent that if either of the dye precursors is exposed to oxygen, then some oxidation is likely to occur, and the hair to which the composition is subsequently applied may not acquire a true dark black color. 2,4-Diaminophenol is particularly prone to autoxidation in this way.

It is therefore necessary to ensure that all or substantially all oxygen is removed from the composition and that access of oxygen is prevented until such a time as the composition is required for dyeing hair.

The ingredients of the composition and the composition itself can be purged of oxygen by preparing and packing the composition in the presence of an inert gas such as for example nitrogen, carbon dioxide or a liquefiable gaseous propellant.

As an alternative, or additional to the use of an inert gas, the composition can contain an antioxidant to scavenge any oxygen that may come into contact with the dye precursors, either during manufacture of the composition or during storage prior to use.

When an antioxidant is employed, suitable antioxidants include, for example, ascorbic acid, sodium metabisulphite and sodium dithionite, or mixtures thereof, which should be employed in the composition in an amount sufficient to scavenge dissolved oxygen or gaseous oxygen enclosed within the headspace above the composition, while the composition is held in a closed container. Such antioxidants or mixtures thereof can usually be employed in the composition at a concentration of from 0.01 to 2%, preferably from 0.1 to 1% by weight of the composition.

It should be explained that where reliance is placed on the use of an antioxidant as an oxygen scavenger, compositions containing less than 0.01% by weight of antioxidant can contain oxygen that may not be fully scavenged by such a low level of antioxidant, whereas compositions containing more than 2% by weight of antioxidant can have their effectiveness diminished when applied to hair, due to interference with the autoxidation reaction on contact with atmospheric oxygen, on which the production of a true dark black color relies.

The compositions according to the invention can optionally also contain detergent, although care should be exercised in the choice and/or quantity of detergent employed, as some tend to reduce the intensity of the black color of the dyed hair, or result in the development of colors other than black.

Suitable detergents for use in the process of the invention can be selected from anionic, non-ionic, amphoteric, zwitterionic and cationic detergents or mixtures of detergents from two or more of these detergent classes.

Examples of anionic detergents include alkyl benzene sulphonates, such as sodium alkyl benzene sulphonates and sodium alkyl naphthalene sulphonates; alkyl sulphates, particularly those having from 12 to 18 carbon atoms in molecule, such as sodium lauryl sulphate and triethanolamine sulphate; alkyl benzene polyoxyethylene sulphonates, particularly those wherein the alkyl radical has from 8 to 12 carbon atoms; sulphated monoglycerides, such as lauric monoglyceride sodium sulphate, lauric monoglyceride ammonium sulphate and sulphated cocomonoglyceride ammonium salt; alcohol ether sulphates; sarcosines, such as lauroyl sarcosine and cocoyl sarcosine; and sulphosuccinates, such as the dioctyl esters of the salts of sulphosuccinic acid.

Examples of cationic detergents include distearyl dimethyl ammonium chloride, dilauryl dimethyl ammonium chloride diisobutylphenoxyethoxyethyl dimethyl benzyl ammonium chloride, cetyl trimethyl ammonium bromide, N-cetyl pyridinium bromide and benzethonium chloride.

Examples of amphoteric detergents include N-alkyl β-imino dipropionates, N-alkyl 8-amino propionates and the basic quaternary ammonium compounds derived from 2-alkyl-substituted imidazoline such as hydroxyethyl carboxymethyl alkyl imidazolinium hydroxide (MIRANOL), especially the lauric, myristic or stearic derivatives.

Examples of nonionic detergents include condensates of ethylene oxide with hydrophobic bases formed by condensing propylene oxide with propylene glycol (PLURONICS), nonyl phenoxypoly-(ethyleneoxy)ethanol (IGEPAL), and polyoxyethylene(20)sorbitan monooleate (TWEEN 80).

Suitable detergents for use in the process of the invention can also comprise soaps which are water soluble salts of higher fatty acids and include alkali metal soaps such as sodium, potassium, ammonium and alkanol ammonium salts of straight chain saturated or unsaturated fatty acids containing from 8 to 24 carbon atoms, preferably from 10 to 20 carbon atoms. Preferred soaps include potassium, monoethanolamine, diethanolamine and triethanolamine soaps of $C_{12}$ to $C_{14}$ fatty acids, particularly of coconut fatty acids.

It has however been shown that when a detergent is to be incorporated into compositions of the invention, the preferred anionic detergent is one chosen from Sodium lauryl ether sulphate (2EO) (such as EMPICOL ESB 3S) and Sodium lauryl ether sulphate (3EO) (such as GENAPOL ZRO).

When a nonionic detergent is employed, it is preferably mixed with an anionic detergent in order to increase foam volume when the composition is applied to the hair, without reducing the intensity of the true dark black color produced. Examples of preferred nonionic detergents are polyoxyethylene lauryl alcohol:23EO (such as BRIJ 35) and oleic diethanolamide (such as MARLAMIDE D 1885).

The preferred detergent mixture comprises sodium lauryl ether sulphate:2EO with either of the above-named nonionic detergents.

The quantity of detergent when employed in the composition, will depend on which detergent is chosen and whether a mixture of detergent is employed. Whereas the use of a detergent assists application of the composition to the hair, in that a foam is produced which enables the user more readily to distribute the composition evenly onto and thoroughly into the hair, care must be exercised that the quantity of detergent is not so excessive that a true dark black hair color does not result.

It is but a simple task to establish a suitable quantity of a detergent for this purpose by experimental application of a series of compositions containing differing amounts of detergent to switches of blond hair, and then selecting that composition which produces the pleasing true dark black color.

However, by way of example with reference to the preferred anionic and nonionic detergents referred to hereinbefore, the quantity of detergent that can be employed in compositions according to the invention is 1 to 15%, preferably from 5 to 10% by weight of the composition, expressed in terms of active detergent.

If less than 1% by weight of any of the preferred anionic or nonionic detergents is employed, then it is unlikely that the consumer, when applying the composition to the hair, will obtain a significant lather from which the advantages of employing a detergent in the composition can be derived. If more than 15% by weight of any of the preferred anionic or nonionic detergents is employed, then application of the composition to the hair may yield an excessive volume of foam and may result in the development of a hair color which is not a true dark black.

Ideally, the composition should contain a mixture of the preferred anionic and nonionic detergents at an active detergent ratio of 1:3.

The composition according to the invention can also optionally contain a thickening agent to enable it to be more easily dispensed from a container in a controlled manner, and more readily applied to the hair without, for example, running off the scalp.

Suitable thickening agents include:
  carboxyvinyl polymers such as CARBOPOL* 940 and CARBOPOL* 941, and
  polyethylene glycol distearate.
*trademark Thickening agents such as these can be employed at a concentration of from 0.1 to 2%, depending on the choice of thickening agent. The Carbopols can, for example, be employed at a concentration of up to about 1% and the polyethyleneglycol derivative up to about 2% by weight.

It is also possible to include in compositions according to the invention other ingredients such as conditioners, polymers, preservatives and perfumes, and other ingredients such as are conventionally employed in products intended for the treatment of hair.

The invention also relates to a process for preparing a composition for use in the dyeing of keratinous fibres to produce a true dark black color, which process comprises the steps of:

(i) dissolving in oxygen-free water the dye precursors 2-methoxy-p-phenylene diamine and 2,4-diaminophenol, the composition having a pH value of from 6 to 12; and (ii) packaging the composition in a closed container in the substantial absence of oxygen.

The pH of the composition so prepared may be adjusted to the desired value of 6 to 12, preferably 7 to 10, by addition of an alkali such as sodium hydroxide or ammonia, or by employing a suitable buffer.

According to a preferred process, the dye precursors are dissolved in an aqueous solution of an antioxidant so as to establish oxygen-free conditions, care being exercised to exclude oxygen, for example by purging with an inert gas.

Optionally, polar organic solvents, such as isopropyl alcohol, may also be added to aid solution of the dye precursors.

The composition should be stored prior to use in a closed container from which it can be readily dispensed when required for application to the hair. The container or dispenser should preferably be one which is airtight or will at least prevent the ingress of atmospheric oxygen sufficient to cause the dye precursors to oxidize prematurely.

Suitable containers include plastic sachets, capped jars or tubes, pump spray operated applicators or pressurized aerosol devices in which liquefiable gaseous propellant can maintain a substantially oxygen-free headspace. The chosen design of the container, dispenser or applicator will depend partly on whether single or multiple dose application is intended, and partly on the means selected for ensuring that the composition is stored in a substantially oxygen-free state.

The preferred closed container is designed to provide a single dose or so-called one pack product, the contents of which are sufficient to dye one head of hair.

The invention also provides a method for dyeing keratinous fibres which comprises applying to the keratinous fibres a composition comprising a substantially oxygen-free solution of 2-methoxy-p-phenylenediamine and 2,4-diaminophenol, and allowing these dye precursors to oxidize in the presence of atmospheric oxygen.

When hair is to be dyed with compositions according to the invention, it is optionally first washed and then a proportion of the substantially oxygen-free solution containing the dye intermediates is applied to damp but not wet hair, to avoid over dilution of the dye precursors, and thoroughly rubbed in. By way of example, for a normal head of hair (about 70 g in weight) about 20 ml of an aqueous solution containing 0.4 M of both the dye precursors is applied to the damp hair. Both the duration and temperature of application to the hair will affect the final result obtained. In general, the longer the time and the higher the temperature of contact, the more intense is the true dark black of the dyed hair which finally results, but 10 to 30 minutes at room temperature (20° to 25° C.) is usually sufficient for the development of a desirably intense true dark black color. Preferably, dyeing to a true dark black color is achieved without employing hydrogen peroxide as is conventional in a two-pack hair dye treatment.

It is also possible to apply repeatedly a dilute solution of the mixture of dye precursors in order to darken light or grey hair gradually until a desirably dark or true dark black color is obtained. As an example, an aqueous substantially oxygen-free solution of 2-methoxy-p-phenylenediamine and 2,4-diaminophenol, each at a concentration of from 1 to 2% by weight can be applied to grey hair once or twice a day for about one week in order to obtain gradual darkening until a true dark black is obtained. Usually, 7 to 8 successive applications are sufficient to develop a good true dark black color to the hair.

Compositions according to the invention are particularly of value in the dyeing of human hair either attached to the head or in the form of a wig, hairpiece or switch. The compositions can however also be employed in the dyeing of natural keratinous fibres such as wool or silk or of synthetic keratinous fibres.

The invention is illustrated by the following Examples of "one-pack" compositions according to the invention containing both 2-methoxy-p-phenylenediamine (MPPD) and 2,4-diaminophenol (DAP).

EXAMPLE 1

In this example a solution of both dye intermediates in the form of their respective salts was prepared in buffer and the solution stored under nitrogen to provide oxygen-free conditions.

Preparation of buffer

Sodium dihydrogen orthophosphate, 13.6 g was dissolved in water, 500 ml, and isopropyl alcohol, 150 ml, was added and the solution made up to 1 litre after adjustment of the pH with sodium hydroxide to 8.0.

Preparation of solution of dye intermediates 76.2 g MPPD (as the sulphate monohydrate salt) together with 19.7 g DAP (as the dihydrochloride salt) were dissolved in 1 litre of the buffer containing antioxidant to provide a concentration of 0.3 M with respect to the MPPD and 0.1 M with respect to the DAP.

This mixed solution was prepared under nitrogen and stored in the absence of oxygen until required for use.

Dyeing of hair

A switch of Italian "Blue String" virgin blond hair (about 1 g) was thoroughly wetted with tap water, excess water removed by blotting with filter paper and immersed in the oxygen-free solution containing the dye precursors in a 5 cm dish open to the atmosphere.

The switch was turned and agitated frequently with a glass rod during dyeing. After immersion for 20 minutes in the dye solution, the hair switch was rinsed and dried.

The switch of hair had a true dark black color.

In control experiments in which first the MPPD was omitted, and then secondly the DAP was omitted, similar switches of blond hair were dyed dark brown and pale blue/black respectively.

EXAMPLE 2

This example illustrates the inclusion of detergents in compositions according to the invention.

The following formulation was prepared as a "one-pack" product.

| Ingredients | % w/w |
| --- | --- |
| Sodium lauryl ether sulphate (2EO) (EMPICOL ESB 3S:25% AD) | 10.0 |
| Thickener Carboxyvinyl polymer (CARBOPOL 940) | 1.0 |
| Dye intermediates | |
| 2-methoxy-p-phenylenediamine: sulphate monohydrate salt (MPPD) | 7.62 |
| 2,4-diaminophenol:dihydrochloride salt (DAP) | 1.97 |
| Solvent for MPPD Isopropanol | 2.0 |
| Antioxidant Sodium metabisulphite | 0.5 |
| pH adjustant to pH 8.5 Ammonium solution | q.s. |
| Water | 100 |

The concentration of MPPD can also be expressed as 0.3 M and that of DAP as 0.1 M.

The above "one-pack" product was successfully stored for four months in the absence of oxygen, without deterioration or loss of viscosity, at temperatures ranging from 0° C. to 50° C.

The product when applied to blond hair dyes it an intense true dark black under conditions described in Example 1.

EXAMPLES 3 AND 4

Example 2 was repeated except that the CARBOPOL 940 thickener at a concentration of 1.0% by weight was replaced firstly with CARBOPOL 941 at a concentration of 0.9% by weight and secondly by polyethyleneglycol 6000 distearate at a concentration centration of 2.0% by weight.

Both of these modified one-pack products stored well without appreciable loss of viscosity under the conditions used in Example 2, and they both successfully dyed blond hair an intense true dark black under similar conditions of use.

EXAMPLES 5 AND 6

Example 2 was repeated except that sodium metabisulphite was replaced either with sodium dithionite (0.5% by weight) or with ascorbic acid (0.5% by weight).

In both cases, hair was dyed true dark black under similar conditions of use.

Experiments

The following experiments illustrate the importance of the defined molar ratios of the dye precursors, the pH of the composition and the duration of contact with hair during the dyeing process.

Experiment A

The procedure described in Example 2 was also repeated except that the concentration of MPPD was 0.5% by weight (0.02 M), and that of DAP was 7.8% by weight (0.4 M). The molar ratio of MPPD to DAP in the composition was accordingly 1:20 which was also well outside the lower limit defined by the invention of 1:10.

Blond hair dyed using this composition was initially dark brown, but after a few days, the hair acquired a distinct redness.

Experiment B

The procedure described in Example 2 was repeated, except that the composition was adjusted to a pH value of 5, which was below the lower limit defined by the invention of 6.

Blond hair dyed with this composition acquired a brown color.

Experiment C

The procedure described in Example 2 was repeated, except that the composition was used to treat a switch of blond hair for only five minutes which was less than the minimum recommended time of 10 minutes.

The switch of hair acquired a brown color.

It was noted from these experiments that in each case a true dark black color was not obtained. This illustrates the importance of employing appropriate concentrations of dye precursors, pH of composition and duration of contact time as defined herein.

What is claimed is:

1. A composition for the dyeing of keratinous fibers to produce a true dark black color, which comprises as the sole dye precursors from 0.25 to 15% by weight of a mixture of 2-methoxy-p-phenylenediamine and 2,4-diaminophenol as an aqueous, substantially oxygen-free solution, the molar ratio of one dye precursor to the other being from 1:10 to 10:1, the composition having a pH value of from 6 tp 12.

2. The composition of claim 1, wherein the dye precursors together form from 1 to 10% by weight.

3. The composition of claim 1, wherein the molar ratio of 2-methoxy-p-phenylenediamine to 2,4-diaminophenol is from 1:5 to 1:3.

4. The composition of claim 3, wherein the molar ratio of 2-methoxy-p-phenylenediamine to 2,4-diaminophenol is from 3:1 to 1:1.

5. The composition of claim 1, wherein the dye precursors each form from 0.1 to 14.9% by weight of the composition.

6. The composition of claim 5, wherein the dye precursors each form from 0.5 to 10% by weight of the composition.

7. The composition of claim 1, wherein the solution is maintained in an oxygen-free condition by the presence of from 0.01 to 2% by weight of an antioxidant selected from the group consisting of ascorbic acid, sodium metabisulphite, sodium dithionite and mixtures thereof.

8. The composition of claim 1, which additionally comprises from 1 to 15% by weight of a detergent.

9. The composition of claim 8, wherein the detergent is an anionic detergent selected from the group consisting of sodium lauryl ether sulphate (2EO), sodium lauryl ether sulphate (3EO), and mixtures thereof.

10. The composition of claim 8, wherein the detergent is a nonionic detergent selected from the group consisting of polyoxyethylene lauryl alcohol (23EO), oleic diethanolamide and mixtures thereof.

11. The composition of claim 1, which additionally comprises from 0.1 to 2% by weight of a thickening agent selected from the group consisting of carboxyvinyl polymers, polyethylene glycol distearate and mixtures thereof.

12. A closed container, dispenser or applicator containing the composition of claim 1.

13. The dispenser of claim 12 which is an aerosol pressurized pack dispenser containing an inert propellant.

14. A method of dyeing keratinous fibres a true dark black color, which comprises the step of applying to the keratinous fibres in the absence of hydrogen peroxide, the composition of claim 1.

* * * * *